(12) United States Patent
Regn et al.

(10) Patent No.: US 7,489,961 B2
(45) Date of Patent: Feb. 10, 2009

(54) MEDICAL EXAMINATION OR TREATMENT APPARATUS

(75) Inventors: Judith Regn, Nürnberg (DE); Reiner Staab, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 108 days.

(21) Appl. No.: 11/373,708

(22) Filed: Mar. 10, 2006

(65) Prior Publication Data
US 2006/0203250 A1  Sep. 14, 2006

(30) Foreign Application Priority Data
Mar. 14, 2005  (DE) .................. 10 2005 001 667

(51) Int. Cl.
*A61B 5/05* (2006.01)
(52) U.S. Cl. ..................................... 600/407
(58) Field of Classification Search ................ 600/437, 600/439; 604/67; 606/1, 34
See application file for complete search history.

(56) References Cited
U.S. PATENT DOCUMENTS

| | | | |
|---|---|---|---|
| 4,731,051 A * | 3/1988 | Fischell ........................ 604/67 |
| 5,086,385 A * | 2/1992 | Launey et al. ................. 700/83 |
| 6,074,388 A | 6/2000 | Tockweiler et al. | |
| 6,790,178 B1 * | 9/2004 | Mault et al. .................. 600/300 |
| 6,805,667 B2 * | 10/2004 | Christopherson et al. ... 600/300 |
| 7,171,277 B2 * | 1/2007 | Engleson et al. ............... 700/2 |
| 7,187,916 B2 * | 3/2007 | Mo et al. ..................... 455/323 |
| 7,187,976 B2 * | 3/2007 | Duncan et al. ................ 607/43 |
| 2005/0080403 A1 * | 4/2005 | Takahashi ....................... 606/1 |
| 2005/0143671 A1 * | 6/2005 | Hastings et al. .............. 600/513 |

FOREIGN PATENT DOCUMENTS
DE  297 23 819 U1  4/1999

* cited by examiner

*Primary Examiner*—Eric F Winakur
*Assistant Examiner*—Michael T Rozanski

(57) ABSTRACT

Medical examination or treatment apparatus, in particular X-ray or CT apparatus, comprising a controlling system controlling the operation of one or more apparatus elements, and at least one mobile operating element which is assigned to the control-ling system and which communicates wirelessly with the control-ling system for operating the examination or treatment apparatus for the transmission of operating signals, there being pro-vided at least one device which operates in a direction-selective and/or frequency-selective manner to modify the operating signals transmitted by the operating element such that a controlling system of examination or treatment apparatus disposed adjacent the examination or treatment apparatus to be intentionally operated is not activated by the modified operating signals or there being provided on the examination or treatment apparatus assigned to the operating element at least one acoustic and/or visual signal transmitter which is actuated when an operating signal is generated by the assigned operating element.

3 Claims, 2 Drawing Sheets

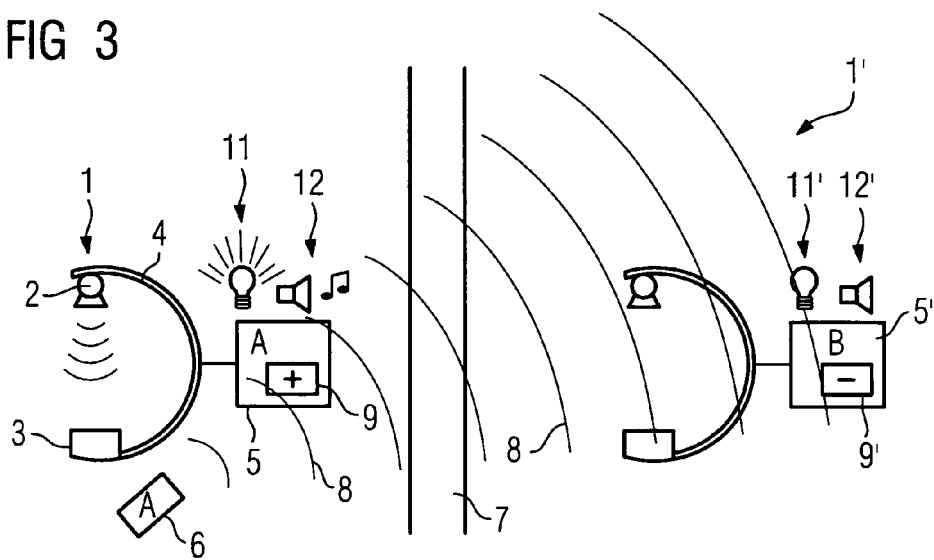
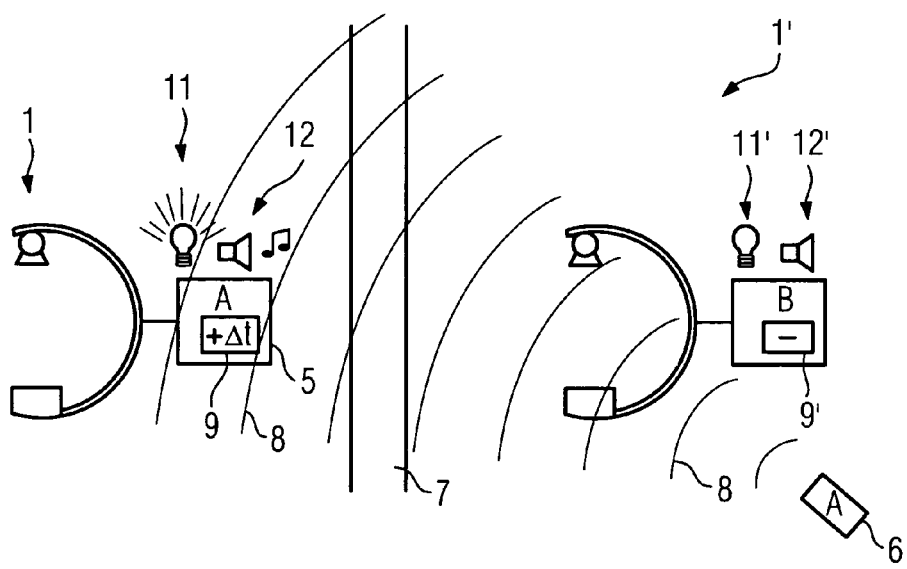

MEDICAL EXAMINATION OR TREATMENT APPARATUS

CROSS REFERENCE TO RELATED APPLICATIONS

This application claims priority to the German Application No. 10 2005 011 667.1, filed Mar. 14, 2005 which is incorporated by reference herein in its entirety.

FIELD OF INVENTION

The invention relates to medical examination or treatment apparatus, in particular X-ray or CT apparatus, comprising a controlling system controlling the operation of one or more apparatus elements, and at least one mobile operating element which is assigned to the controlling system and which communicates wirelessly with the controlling system for operating the examination or treatment apparatus for the transmission of operating signals.

BACKGROUND OF INVENTION

Conventional examination or treatment apparatus, for example an X-ray system, consists of a plurality of spatially separate components such as a patient positioning table, an X-ray source ceiling stand and/or an X-ray source floor stand and a wall stand or a C-arm. Conventionally provided in addition is a controlling system comprising image processing apparatus, the controlling system activating the operation of the apparatus elements to be activated; in the case of X-ray apparatus this is, for example, the generator which provides the high voltage required to generate the X-rays. The examination or treatment device is thus operated centrally at the controlling system, which has appropriate input options in the form of switches, keys, joysticks etc.

SUMMARY OF INVENTION

To enable the physician or medical staff additionally to operate at least some of the apparatus elements that are to be activated from a position other than directly by means of the controlling system itself (which has to be done, for example, if the physician or the operator has to be directly with the patient because of the need for further parallel examinations), it is known to provide a wireless mobile function actuator, for example in the form of a foot switch or a hand-held switch which the physician can move or carry with him. A wirelessly communicating operating element of this kind therefore permits, first, operation from a position remote from the controlling system, but naturally also operation when the operator is at the controlling system itself, for example in the case of a foot switch which communicates wirelessly with the controlling system.

The transmission range of known mobile function actuators is generally a few meters. Within this range, the controlling system is guaranteed reliably to receive the appropriate operating signals from its assigned operating element and to be able to actuate the functions or the like thereby defined. The option of carrying the operating element from place to place, in particular in the case of a mobile hand-held device, poses the problem whereby the physician or operator may take the operating element with him and go into another room where there is likewise an X-ray device, for example, but one which would have to be operated with an assigned operating element of its own. This means that mix-ups can occur over which operating element is to be used, possibly leading in turn to the unintentional actuation of functions. A physician carrying with him operating element A assigned, for example, to X-ray device A is standing in front of X-ray device B located, for example, in the next room, and he wishes to actuate a function on X-ray device B. Owing to the ample communication range of operating element A, he now actuates the appropriate function on device A, in front of which he is not standing, while X-ray device B is not activated. The physician does not have sight of X-ray device A so, in respect of that device, there can, for example, be unintentional radiation generation and exposure to radiation or, for example, the patient positioning bed may be unintentionally moved, etc.

DE 297 23 819 U1 discloses a wirelessly communicating foot switch where an already coded signal is transmitted, via a switching signal conversion step, to a slave station assigned to a medical device. The appropriate transmitters of different wirelessly communicating operating devices of a single system have to be of different designs, since differently coded transmit signals are to be generated so that said signals can likewise not influence each other.

An object of the invention is therefore to improve the safe operation of medical examination or treatment apparatus that can be operated by means of mobile, wirelessly communicating operating elements.

To achieve this object, in the case of medical examination or treatment apparatus of the type referred to at the beginning, according to the invention there is provided at least one device which operates in a direction-selective and/or frequency-selective manner to modify the video signals transmitted by the operating element such that a controlling system of examination or treatment apparatus disposed adjacent the examination or treatment apparatus to be intentionally operated is not activated by the modified operating signals, or there is provided on the examination or treatment apparatus assigned to the operating element at least one acoustic and/or visual signal transmitter which is actuated when an operating signal is generated by the assigned operating element.

According to the invention, there are proposed two equivalent options for improving the safety of the wireless operation of examination or treatment apparatus. According to the first alternative of the invention, the operating signals are deliberately modified or noisy so that, when the situation allows, only the assigned controlling system is activated but not the controlling system of adjacent examination or treatment apparatus disposed, for example, in another room. The direction-selective or frequency-selective device of this kind used can, for example, be a scrambler, which is preferably integrated into a building wall and operates in a direction-selective and/or frequency-selective manner such that operating signals generated on the near side of the building wall, after passing through the building wall, continue to be propagated in a modified state on the far side thereof, and thus no longer incorporate any control information that can lead to inadvertent incorrect actuation.

Within the scope of this alternative of the invention there are two separate cases. In the first case the operator is located, for example, in front of X-ray apparatus A and is holding operating element A in his hand. Should he now wish, for example, to actuate image acquisition, that is to say the generation of radiation, he will actuate the appropriate button or switch on operating element A, which communicates wirelessly with the controlling system of X-ray apparatus A, which system starts the generation of radiation. Owing to the considerable transmission range of the operating element, there is now the risk that the operating signals will, for example, pass through a building wall separating two rooms and pass into the receiving range of X-ray apparatus B standing in that room or the controlling system of said apparatus. Where said controlling system has, for example, a receiver that operates over an adequately broad bandwidth, said controlling system could treat the operating signals as actuating signals and, for example, likewise start the image acquisition operation. However, the use of the signal-modifying device, that is to say for example, the scrambler, for example in the building wall, enables this to be advantageously avoided since the operating signals generated on the near side of the wall are modified by the scrambler and are supplied on the far side, if at all, in a form that renders function actuation impossible. Inadvertent incorrect operation of X-ray apparatus B on the basis of the considerable transmission range of operating element A is thus precluded.

Conversely, in the second case, the operator is standing with operating element A in front of X-ray device B and wishes to activate said device using operating element A. Since the communication frequencies are normally within a relatively narrow bandwidth, as a rule it will not be possible to activate X-ray apparatus B using operating element A. Owing to the considerable radio transmission range, however, the operating signals may pass through the building wall and into the adjacent room in which apparatus A is disposed, and said signals may be received by the controlling system which activates the appropriate actuation of, for example, the image acquisition operation. This is naturally unintentional and can be advantageously prevented by the use of the one or more scramblers integrated into the building wall.

According to the second alternative of the invention, the operator is to be actively signaled to indicate whether or not he is standing in front of the controlling system assigned to the operating element. To this end, the examination or treatment apparatus is provided with at least one acoustic or visual signal transmitter, for example in the form of a tone generator or flashing light or the like. If the operator with the mobile operating element is standing in front of the assigned controlling system, that is to say, wishes to operate the "correct" apparatus, communication can be successfully set up between the operating element and the controlling system. If that is the case, the controlling system activates the acoustic/visual signal transmitter. The operator is therefore given an AF signal or a blinking signal which shows him that he is standing in front of the correct controlling system and can thus readily operate the apparatus. Were he to be standing in front of the wrong device, communication between the operating element and the controlling system could not be set up since, as a rule, these two have different communication frequencies. Thus it is also impossible for any acoustic/visual signal to be generated.

In this context it is useful if the operating element transmits an identification signal to the controlling system along with the operating signals, that is to say, identifies itself to said system, the acoustic/visual signal being generated only once the controlling system has verified and identified the operating element. This means that the actuating moment for the generation of the acoustic/visual signal is not only the fact that the operating element and controlling system are able to intercommunicate but rather solely the fact that the operating element identifies itself to the controlling system. As a result, if the receiver in the controlling system receives over a relatively broad bandwidth, that is to say there is not necessarily any frequency-based separation, then no acoustic/visual signal will be transmitted only on the basis of the fact that the operating element and controlling system are able to intercommunicate, yet the operator is standing in front of the wrong device. Since in this case, however, the operating element cannot identify itself to the controlling system, signal generation is also safely prevented in such a case.

Since the problem of the considerable transmission range exists in this case too, and since it is therefore possible for the operator standing in front of, for example, the wrong X-ray apparatus to operate the X-ray apparatus in the adjacent room unintentionally owing to the considerable transmission range, it is useful if the controlling system assigned to the operating element processes the operating signals arriving from its assigned operating element only following expiry of a predetermined period of time. In this case the operator, who is not given an acoustic/a visual check-back signal because he is standing in front of the wrong device, thus still has enough time, after discovering the situation, immediately to stop the unintentional operation of the controlling system located in the adjacent room, for example by means of a stop switch or emergency stop switch on the operating element which, owing to the radio transmission range, can directly access the associated X-ray apparatus located in the adjacent room in this case too.

BRIEF DESCRIPTION OF THE DRAWINGS

Further advantages, features and details of the invention will emerge from the exemplary embodiments described below and with reference to the drawings, in which:

FIG. 3 is a schematic sketch of an operating situation using visual/acoustic signal transmitters, and FIG. 4 is a further operating situation corresponding to FIG. 3.

DETAILED DESCRIPTION OF INVENTION

Figure 1:
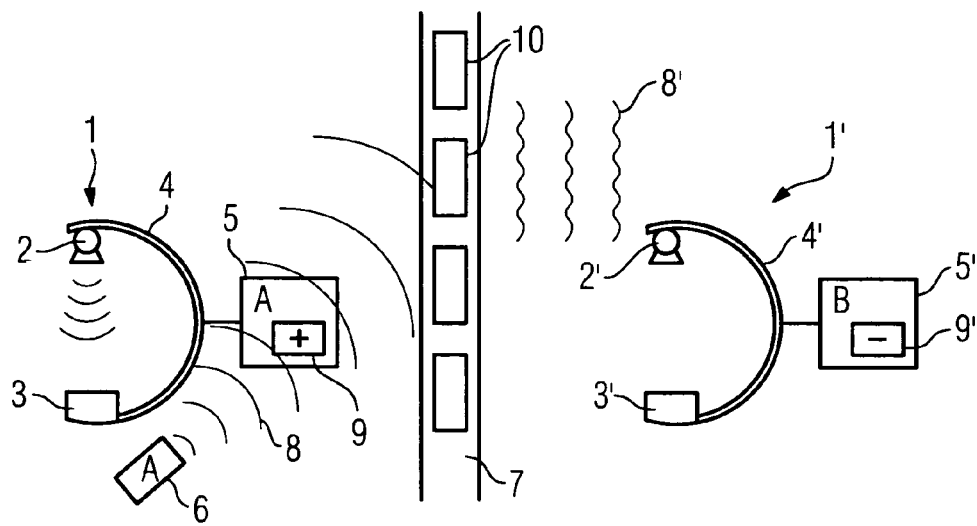
FIG. 1 is a schematic sketch of a first operating situation using signal-modifying devices.

FIG. 1 shows first examination or treatment apparatus 1, in this case in the form of a C-arm X-ray device, comprising a source of radiation 2 and a radiation detector 3 which are disposed on a common C-arm 4. There is also an associated central controlling system 5. The structure of X-ray apparatus of this kind is sufficiently well known; FIG. 1 is merely a schematic sketch, and the individual components are not important.

Assigned to the controlling system 5 is a mobile operating element 6, for example a hand-held transmitter, which enables remote communication to take place with the controlling system 5 in order to actuate functions. The wireless communication can take place in any manner, for example by means of radio, Bluetooth, etc.

In an adjacent room, separated by a building wall 7, there is located further examination or treatment apparatus 1', also shown here by way of example as X-ray apparatus, comprising a source of radiation 2', a radiation detector 3', a C-arm 4' and a controlling system 5'.

If the physician or an operator wishes to actuate image acquisition via the X-ray apparatus 1, he can do so using the mobile operating element 6. Said element emits operating signals 8 which are received by a receiver 9, which is integrated into the controlling system 5 and which evaluates said signals and thus enables the controlling system 5 to activate the appropriate components, in this case the generator for generating the high voltage for operating the source of radiation 2. In the example shown, the operating signals 8 are propagated towards the building wall 7 and pass through it. In the example shown, however, there are integrated into the building wall 7 a plurality of devices in the form of scramblers 10, which modify or corrupt the operating signals 8 so that, on the far side of the building wall 7, that is to say in the room where the apparatus 1' is located, only modified, corrupted operating signals 8' continue to be propagated. These are not capable of being either received or evaluated by the receiver 9' of the controlling system 5'. This therefore prevents the possibility of adjacent apparatus from being inadvertently incorrectly operated despite the considerable transmission range of the operating signals 8 of the operating element 6. The non-reception of the modified operating signals 8' by the receiver 9' is represented by the "−" symbol in the receiver 9', while the correct activation of the controlling system 5 is represented by the "+" symbol in the receiver 9. The assignment of the operating element 6 to the controlling system 5 is, moreover, represented by the symbol "A", while the controlling system 5' is indicated by the symbol "B".

Figure 2:
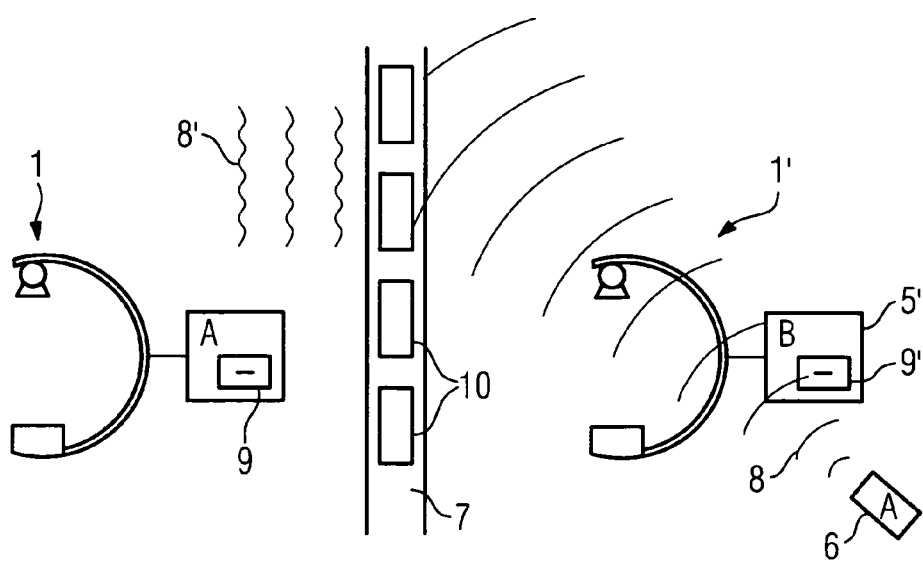
FIG. 2 is a schematic sketch, corresponding to FIG. 1, of a second operating situation.

FIG. 2 shows a further operating situation where the physician or operator has inadvertently taken the operating element 6 with him into the examination room in which the examination or treatment apparatus 1' is disposed. He actually wishes to operate the apparatus 1', but this is not possible using the operating element 6 assigned to the apparatus 1, for example because the receiver 9' receives only signals of a frequency other than that of the operating signals 8. This means that it is not possible to activate the apparatus 1', as indicated by the "−" symbol in the receiver 9'. In theory, however, the apparatus 1 could be activated if the operating signals 8 were to pass unmodified through the building wall 7. Here too that is, however, prevented by the scramblers 10 which are integrated into the wall and which permit only modified or corrupted operating signals 8' to be propagated further. These signals, in turn, cannot be received by the receiver 9, as indicated by the "−" symbol. Unintentional operation of the apparatus 1, which the physician cannot see because he is in the adjacent room, is thereby advantageously precluded.

FIG. 3 shows a situation corresponding to that in FIG. 1, and to this extent the same reference characters are used. In this case, however, the physician is actively alerted to the fact that he is standing in front of the correct controlling system 5, that is to say, he can actually operate the apparatus 1 using the operating element 6. In the example shown, a visual signal transmitter 11 and an acoustic signal transmitter 12 are provided at the controlling system for this purpose. If, for example, the source of radiation 2 is to be used, the receiver 9 receives the operating signals 8 transmitted by the operating element, as represented by the "+" symbol. Together with the operating signals it is, for example, also possible for an identification signal to be transmitted by which the operating element 6 identifies itself to the controlling system 5 as the assigned element. If communication has therefore been successfully achieved and, where appropriate, the identification signal has also been detected, the visual signal transmitter 11, represented by the lamp symbol, is activated and a blinking signal is thus generated. The acoustic signal transmitter, represented by the loudspeaker, can also be activated alternatively or parallel thereto, with the result that the physician is also given an AF signal. He therefore knows that he is standing in front of the right operating apparatus.

Here again the operating signals 8 pass through the building wall 7 and, since no scramblers are provided with this embodiment, said signals arrive unmodified at the controlling system 5'. However, for example the receiver 9' receives only signals of another frequency, which is why in this case inadvertent operation of the apparatus 1' is precluded, as represented by the "−" symbol in the receiver 9. Should the receiver 9 receive over a relatively broad bandwidth, inadvertent incorrect operation could be conclusively precluded in this case by provision for an identification signal also to be transmitted and for the apparatus 1' to be operated only if calibration of the identification signal indicates that the assigned operating element is generating the operating signals. In the example shown, this would be the case if an operating element "B" (not shown in further detail) were to generate the signals. In any event, operation of the apparatus 1' is not possible, and the signal transmitters 11', 12' are not activated.

FIG. 4 shows the situation where the physician again inadvertently takes the operating element 6 with him into the room in which the apparatus 1' is disposed. Here again the operating signals 8 are not received by the receiver 9' or in any event are not processed, as represented by the "−" symbol. The physician does not receive any feedback via the signal transmitters 11', 12' since these are not activated; that is to say, the flashing light does not flash, and the AF signal is not generated. The physician thus realizes immediately that he is not standing in front of the correct apparatus.

Here again the operating signals 8 pass through the building wall 7, are received by the actually assigned "correct" receiver 9 and can be processed, as represented by the "+" symbol. The visual signal transmitter 11 is activated and flashes; the acoustic signal transmitter is activated and generates an AF signal. In theory, the operating signal would now be processed immediately, for example radiation would be generated. However, the signal transmitters 11', 12' are giving the physician no feedback, so he knows that he is in the wrong room or has the wrong operating element 6 in his hand. To enable him to halt operation of the apparatus 1 in time, the operating signal is processed only after expiry of a time lag Δt, as indicated in the receiver 9. During this time the physician can, for example, go into the room in which the apparatus 1 is disposed to halt the operation directly at the controlling system 5. Alternatively he can, of course, also do this using the operating element 6, on condition that said element is provided with, for example, an emergency stop switch. After all, as stated, the operating signals 8 pass through the building wall 7 and can be received by the receiver 9 and, when an emergency stop signal is generated, the system stop is naturally processed without skew.

The invention claimed is:

1. A medical examination or treatment apparatus, comprising:
   a controlling system for controlling one or more apparatus elements in a first examination or treatment apparatus located in a first room;
   at least one mobile operating element assigned to the controlling system and configured to communicate wirelessly with the controlling system for operating the first examination or treatment apparatus by transmitting operating signals; and
   at least one processing device configured to operate direction-selectively and/or frequency-selectively for modifying the operating signals transmitted by the operating element such that a second controlling system of a second examination or treatment apparatus arranged in a second room adjacent to the first room is not activated by the modified operating signals, wherein the direction-selective and/or frequency-selective device is a scrambler integrated into a building wall between the first and the second rooms, wherein the scrambler is configured to receive at least one of the following signals: a first operating signal intended just for operation of the first examination or treatment apparatus yet capable of causing an unintended operation of the second examination or treatment apparatus, the first operating signal passing through the building wall from the first room to the second room, and a second operating signal intended just for operation of the second examination or treatment apparatus yet capable of causing an unintended operation of the first examination or treatment apparatus, wherein the scrambler is further configured to modify a received first operating signal and a received second operating signal as each respective one of the first and second operating signals passes through the building wall so that the modified first operating signal is disabled from operating the second examination or treatment apparatus as said modified first operating signal propagates to the second room, and further so that the modified second operating signal is disabled from operating the first examination or treatment apparatus as said modified second operating signal propagates to the first room.

2. The examination or treatment apparatus according to claim 1, wherein the controlling system is configured to process the operating signals transmitted by the operating element only after lapse of a selectable dead time.

3. The examination or treatment apparatus according to claim 1, wherein the operating element is a portable or movable foot switch or a portable hand-held switch.

* * * * *